United States Patent [19]
Bishopp

[11] Patent Number: 5,341,992
[45] Date of Patent: Aug. 30, 1994

[54] CONTAINER

[75] Inventor: Derek A. Bishopp, Woodbridge, England

[73] Assignee: The Beautiful Bouquet Company Limited, England

[21] Appl. No.: 922,359

[22] Filed: Jul. 29, 1992

Related U.S. Application Data

[63] Continuation-in-part of Ser. No. 678,964, Apr. 22, 1991, abandoned.

[30] Foreign Application Priority Data

Oct. 22, 1988 [GB] United Kingdom .............. 8824799.4
Dec. 3, 1988 [GB] United Kingdom .............. 8828288.4

[51] Int. Cl.⁵ .............................................. A61L 9/04
[52] U.S. Cl. ......................................... 239/34; 239/55
[58] Field of Search ........................ 239/34, 36, 52, 53, 239/55, 56, 57

[56] References Cited

U.S. PATENT DOCUMENTS

| | | |
|---|---|---|
| 1,871,419 | 8/1932 | McKee . |
| 2,615,754 | 10/1952 | Lindenberg . |
| 2,626,833 | 1/1953 | Valentine . |
| 2,639,939 | 5/1953 | Matchett . |
| 2,717,174 | 9/1955 | Casanovas . |
| 2,728,604 | 12/1955 | Garfield . |
| 2,946,511 | 7/1960 | Bartus . |
| 2,988,283 | 6/1961 | Garfield . |
| 3,185,394 | 5/1965 | Farrell . |
| 3,216,882 | 11/1965 | Feldt . |
| 3,575,345 | 4/1971 | Buck, Jr. . |
| 3,685,734 | 8/1972 | Paciorek . |
| 3,711,024 | 1/1973 | Hammond . |
| 3,785,556 | 1/1974 | Watkins . |
| 3,815,828 | 6/1974 | Engel . |
| 3,896,995 | 7/1975 | Lelicoff . |
| 4,094,119 | 6/1978 | Sullivan . |
| 4,145,001 | 3/1979 | Veyenberg et al. . |
| 4,202,472 | 5/1980 | Lin . |
| 4,277,024 | 7/1981 | Spector . |
| 4,283,011 | 8/1981 | Spector . |
| 4,419,395 | 12/1983 | Sugimoto . |
| 4,513,862 | 4/1985 | Mallow . |
| 4,634,614 | 1/1987 | Holzner . |
| 4,696,393 | 9/1987 | Laipply . |
| 4,720,417 | 1/1988 | Sweeny . |
| 4,751,934 | 6/1988 | Moir et al. . |

(List continued on next page.)

FOREIGN PATENT DOCUMENTS

| | | |
|---|---|---|
| 692754 | 7/1967 | Belgium . |
| 0004463 | 10/1979 | European Pat. Off. . |
| 0161091 | 11/1985 | European Pat. Off. . |
| 0188883 | 7/1986 | European Pat. Off. . |
| 0189656 | 8/1986 | European Pat. Off. . |
| 0215480 | 3/1987 | European Pat. Off. . |
| 0283621 | 9/1988 | European Pat. Off. . |
| 0307551 | 3/1989 | European Pat. Off. . |
| 0349184 | 1/1990 | European Pat. Off. . |
| 0367581 | 5/1990 | European Pat. Off. . |
| 0441034 | 8/1991 | European Pat. Off. . |
| 525530 | 2/1993 | European Pat. Off. . |

(List continued on next page.)

Primary Examiner—Andres Kashnikow
Assistant Examiner—Christopher G. Trainor
Attorney, Agent, or Firm—Charles D. Gunter, Jr.

[57] ABSTRACT

The present invention provides a storage container containing one or more packets of toilet paper. The container is adapted to have at least part of a wall thereof removed to permit access to the contents of the container for removal thereof from the container and is provided with a device located on or adjacent an outer face of the container wall for preferentially releasing a scent or other volatile material externally of the container into the environment of the container and substantially not into the interior of the container. Preferably, the volatile material releasing device is adapted to be actuated to release the material prior to removal of the container wall to permit access to the contents of the container. The invention also provides a disc or the like carrying the volatile material enclosed thereon by a removable cover foil.

14 Claims, 2 Drawing Sheets

U.S. PATENT DOCUMENTS

| | | |
|---|---|---|
| 4,837,421 | 6/1989 | Luthy . |
| 4,848,929 | 7/1989 | Rawl . |
| 4,874,129 | 10/1989 | DeSapio . |
| 4,880,690 | 11/1989 | Szycher . |
| 4,923,063 | 5/1990 | Tararuj . |
| 4,941,574 | 7/1990 | Meehan . |
| 4,957,246 | 9/1990 | Kantor . |
| 4,998,621 | 3/1991 | Meehan . |
| 5,161,688 | 11/1992 | Muchin . |
| 5,170,938 | 12/1992 | Dewing . |

FOREIGN PATENT DOCUMENTS

| | | |
|---|---|---|
| 86/00430 | 6/1987 | France . |
| 57-52457 | 3/1982 | Japan . |
| WO92/14607 | 9/1992 | PCT Int'l Appl. . |
| 430577 | 6/1935 | United Kingdom . |
| 618311 | 2/1949 | United Kingdom . |
| 736221 | 9/1955 | United Kingdom . |
| 758686 | 10/1956 | United Kingdom . |
| 763681 | 12/1956 | United Kingdom . |
| 887478 | 1/1962 | United Kingdom . |
| 1370282 | 10/1974 | United Kingdom . |
| 1516845 | 7/1978 | United Kingdom . |
| 2005141 | 4/1979 | United Kingdom . |
| 2158356A | 11/1985 | United Kingdom . |
| 2168031 | 6/1986 | United Kingdom . |
| 2226982 | 7/1990 | United Kingdom . |

CONTAINER

The present application is a continuation-in-part application of Ser. No. 07/678,964, filed on Apr. 22, 1991.

The present invention relates to a container, notably to a scented container for rolls of toilet paper, and to a means carrying a volatile material for application to that container.

BACKGROUND TO THE INVENTION

Rolls of toilet paper are typically sold in packs containing two, four or more rolls so that the purchaser has to store the rolls which are not immediately required, usually in an unwrapped condition once the outer wrapping for the packs has been removed to gain access to the first roll. However, in the interests of economy, the packaging for such packs of toilet rolls is flimsy and often has no aesthetic appeal. The spare rolls are therefore stored out of sight and often not within immediate reach of the toilet where they are required. For example, they may be stored under a kitchen sink or in an airing cupboard. However, such locations are often under conditions which adversely affect the quality of the tissue paper from which the toilet paper is made.

The manufacturers of such paper impose strict quality controls on moisture and on chemicals in the paper so that it is acceptable to touch and does not bring potentially hazardous chemicals into contact with sensitive skin. However, when stored by the user much of the quality control is negated, for example when unwrapped toilet rolls are stored in the immediate vicinity of bleach or other strong chemical or abrasive cleaners. Where an unwrapped roll is stored adjacent a hot water cylinder, the paper loses up to 5% of its weight in 12 hours as the moisture required to retain its soft texture evaporates.

It has been proposed to impregnate toilet paper with a scent composition, but this requires a change to the conventional toilet paper manufacturing techniques. It has also been proposed to incorporate a scent sachet or block into a toilet paper pack to impart a scent to the paper, see for example U.S. Pat. Nos. 3,711,024 and 4,513,862. However, the scent composition was either in direct contact with the toilet paper or was located so that it would permeate preferentially into the interior of the paper container rather than into the environment, so as to impart scent to the paper as it was being used.

Scent compositions typically contain aromatic oils and anti-oxidants and these can be strongly absorbed by toilet paper if they are allowed to come into contact with the paper. As a result, such impregnated papers could give rise to allergic reactions and discomfort for a user of the paper.

Furthermore, by impregnating the toilet paper itself or by locating the scent carrier inside the packing for the paper, the scent is only available after the package has been opened. As a result, such packages can not be used both to retain the characteristics of the paper, such as moisture content, and the integrity of the package against intrusion from chemicals in the environment (which require that the package remain closed); and to permit escape of a scent into the environment during storage prior to use (which requires that the package be opened). As a result, there is no incentive for a user to store a spare roll in the toilet since it could not release its scent until actually in use.

In British Patent No. 430,577 there is described a toilet paper holder which incorporates a perforated holder for a scent block which allows scent to permeate both onto the paper during use and into the environment around the holder. However, such a holder does not form part of the packaging for the toilet paper and requires that the packaging around the paper be at least partially removed prior to insertion of the paper into the holder. As a result, not only is the paper exposed during use to the scent composition, with the attendant risk of contamination of the paper, but the scent holder does not form part of the packaging within which the toilet paper is sold and stored prior to use, thus requiring that the holder be purchased as a separate item. Again, there is no incentive for a user to store a spare packet of toilet paper in the toilet.

I have devised a form of package for a toilet roll which reduces the above conflicting problems with existing designs and enables a toilet roll to be stored prior to use under controlled conditions (thus preserving its quality and protecting it against contamination), which can be made visually attractive and releases a scent into its environment prior to use (thus providing an incentive to a user to store a spare toilet roll in the toilet) without the need for the user to purchase anything other than the toilet roll and it packaging.

SUMMARY OF THE INVENTION

Accordingly, the present invention provides a flexible walled storage and transport container for a material, which container is adapted to have at least part of a wall thereof removed prior to use of the material so as to form an aperture to permit access to the material within the container for removal of the material from the container, characterized in that the material within the container is one or more packs of toilet paper, in that the container is provided with a volatile material releasing means having no mechanical moving parts and adapted to release the volatile material externally of the container into the environment of the container, and in that said means is located on or adjacent an outer wall of the container whereby it is adapted to release the volatile material substantially only externally of the container and substantially not into the interior of the container.

Preferably, such volatile material releasing means is adapted to be actuated to release the material prior to removal of the container wall to permit access to the contents of the container.

Preferably, the container is made from a flexible material, notably a cardboard, card or paper or a sheet polymer; and in a preferred form comprises a paper, sheet plastic or similar wrapping around a roll of toilet paper; and the means for releasing the scent or other volatile material is carried on or at the exterior surface of the wrapping and is provided with means whereby release of volatile material from the means can be actuated by a user when the container is exposed to a desired environment.

The term packet of toilet paper is used herein in general terms to denote any unitary package containing sheets of toilet paper. The term thus includes generally square or rectangular packs of interleaved single sheets of toilet paper, facial tissues or other absorbent papers, as well as generally cylindrical rolls of toilet paper. For convenience, the term toilet paper will be used herein to denote in general such products and the invention will be described hereinafter in terms of a conventional perforated roll of toilet paper, notably a roll of absorbent tissue paper.

The container of the invention can take a wide range of forms, for example tubular containers or boxes adapted to hold a number of rolls or blocks of interleaved sheets. For example, the invention can be applied to a generally rectangular box-like container adapted to hold one, two or three rolls of toilet paper. Alternatively, the container can be provided as a paper or similar wrapper around the roll or rolls of toilet paper.

However, the invention is of special use with toilet rolls each contained in an individual paper or plastics film wrapping. Such toilet rolls can be contained in an outer wrapping, for example a plastic outer bag from which the individual rolls are removed prior to placing in the toilet; or each individual wrapping can carry a removable cover or secondary wrapping which is removed to activate the release of scent from the scent release means as described below.

It is preferred that the container totally enclose the toilet roll(s) and be generally closed so that the individual rolls are maintained in a controlled environment until unwrapped for use and so that the scent released from the scenting means carried by the container can not penetrate to any significant into the contents of the container. Thus, in a preferred form, the container takes the form of a paper or sheet plastic sleeve around the roll of paper having its open ends gathered together to form a substantially closed wrapping around the roll. The open ends are closed, for example by being stuffed into the open ends of the cardboard tube upon which such rolls are typically wound. A paper or similar disc held in place by a suitable adhesive is affixed to the wrapping across the open ends of the tube to retain the wrapping in position. Such a sleeve is typically formed by wrapping a sheet of paper around the roll so that the edges of the sheet overlap along an axial line along the roll. If desired adhesive can be applied along part or all of the overlap to retain the wrapping in the form of a sleeve. Although such a form of wrapping is not completely air-tight, I have found that such wrapping is acceptable for present purposes. Alternatively, a thermoplastic sheet material can be used as the wrapping material and the overlaps and joints heat sealed together to provide improved air-tightness to the container. If desired, such a thermoplastic material can be heat shrunk upon the toilet roll.

The container for the roll(s) of toilet paper is provided with a means for releasing a scent preferentially into the environment around the container so that little or none of the scent composition or its carrier medium contacts the toilet paper within the container, notably before the container is opened to permit access to the contents for use.

The source of scent for use in the containers of the invention can take the form of a slow release card, paper or other carrier medium impregnated with the desired scent which is affixed to an outer surface of a wall of the container, for example as a paper or microporous plastic disc or other shaped panel impregnated with an oil based scent composition or to which such a scent has been applied as a fluid spray or coating. Alternatively, the scent can be incorporated into the wall of the container during its fabrication, e.g. by using a card or paper impregnated with the appropriate scent composition for part or all of an outer surface of the container wall.

If desired, the source of the scent can be incorporated in a form which requires physical rupture of a part of the container in order to release the scent. Thus, the scent composition could be encapsulated in a suitable wax or polymer coating to give a particulate composition which can be applied to part or all of the container wall. The scent is released upon rupturing of the coating, for example by the peeling action of removing a panel or cover affixed over the coated area, when it is desired to activate the release of the scent. The panel or cover may also serve as the closure to the container and its removal permits access to the container for removal of the contents of the container whilst the scent is released during use of the contents. In this case it will be preferred that the volatile material is located some distance, typically 2 to 5 cms, from the aperture formed in the container wall so that little or none of the volatile material enters the container to contaminate the contents.

The compositions and methods of manufacture of slow or delayed release scent compositions are known in the art and such methods and compositions can be used in the present invention.

Where the scent would otherwise be released to the environment, for example where a scent impregnated disc, it will be desirable to provide some means by which the release of the scent can be delayed until the container is placed into the environment into which the scent is to be released. This can be achieved in a number of ways, for example by applying a foil or similar tear off cover over the scent impregnated or coated area of the container, at least part of which cover is removed to activate release of the scent.

Thus, in a preferred form, the invention provides a container where the volatile material is impregnated onto or applied as a fluid coating to a generally planar carrier substrate which can then be applied to the exterior of a wall of the container, the substrate being provided with a closure member overlying at least the area impregnated or coated with the volatile material to provide a closure which wholly encloses the volatile material and which can be at least in part removed by a user in order to permit release of the volatile material from the substrate.

Alternatively, the container can be packaged in a secondary wrapping which is removed to exposed the container and thus permit release of the scent from the wall of the container. For example, a number of the containers of the invention can be packaged in a polyethylene or similar outer wrapping having a tie or similar re-usable closure to permit individual containers to be removed, whilst retaining a substantially scent-tight enclosure for the remaining containers. Since each container is substantially air-tight, the toilet paper within it is not exposed until the container is removed to gain access to the contents.

As stated above, the volatile material is released preferentially into the environment around the container and not significantly into the interior of the container. This can be achieved as described above by providing the volatile material in or on the external surface of the wall of the container or on a carrier disc or strip affixed to the exterior of the container or as an external coating applied to the container. In order to minimise penetration of the volatile material or its carrier medium through the wall of the container it may be desirable to provide a plastic sheet or other vapour barrier member between the volatile material and the container wall.

Thus, where a scented disc is applied, this will usually carry the scent applied to a vapour impervious backing sheet, or the wall of the container can be coated with a suitable plastic film forming composition, eg. a wax or resin solution, over the area to which the scent has been applied or incorporated into the wall.

The container walls can be printed with suitable decorative motifs or panels so that the container presents an attractive external appearance to the observer.

The container can be manufactured using conventional techniques. If desired, the container can incorporate other features to enhance its utility. Thus, the walls of the covers which are to be removed to release the scent can be formed with apertures having foldable flaps or louvres, which can be opened or closed to provide a measure of control of the release of the scent into the surroundings.

The container of the invention provides a means by which a toilet roll can be stored in a controlled environment prior to use, thus retaining the quality intended by the manufacturer, in a visually attractive and distinctive form which will promote the manufacturer's image and which will provide a source of scent to combat odours at the same time, thus encouraging the user to have a spare toilet roll accessible in the toilet.

If desired, one or more containers of the invention can be incorporated into a conventional multiple pack of toilet rolls so that a purchaser is provided with one or more prepacked containers suitable for storage for future use, together with one or more toilet rolls ready for immediate use.

Accordingly, the present invention also provides a unitary package comprising one or more containers of the invention each containing a toilet paper roll, optionally in association with one or more toilet paper rolls not contained in a container of the invention; the whole being contained within a substantially vapour impervious outer wrapping, notably a plastics or similar outer wrapping.

As indicated above, the containers of the invention can be made using conventional techniques and materials so that the invention can readily be achieved without significant disruption of existing toilet roll manufacturing and packing lines. This is especially the case where the container is wrapped in a conventional paper wrapper to which a scent disc is subsequently applied.

The invention has been described above in terms of a container for a roll of toilet paper. However, it will be appreciated that the paper need not be intended for use on the toilet, but could be any tissue paper for use upon the person. Thus, the invention can be applied to boxes of face tissues or paper handkerchiefs. Furthermore, the volatile material to be released into the environment of the container need not be merely to combat odours. Thus, the material may contain a medicament, eg. menthol or eucalyptus oil, and the term scent as used herein is to denote any volatile material which it is desired to release into the environment of the container.

DESCRIPTION OF THE DRAWINGS

The invention will be described by way of illustration with respect to two forms of container as shown in the accompanying drawings in which.

DESCRIPTION OF THE PREFERRED EMBODIMENTS

Figure 1:
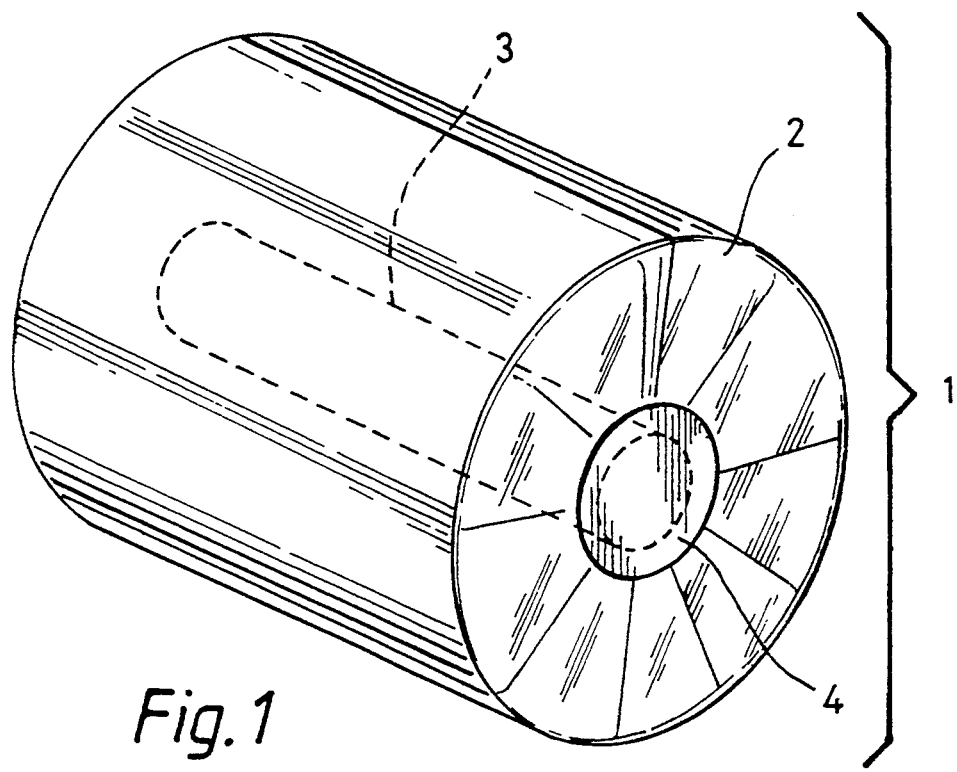
FIGS. 1 and 3 are perspective views of a toilet roll and a box of tissues respectively.
Figure 2:
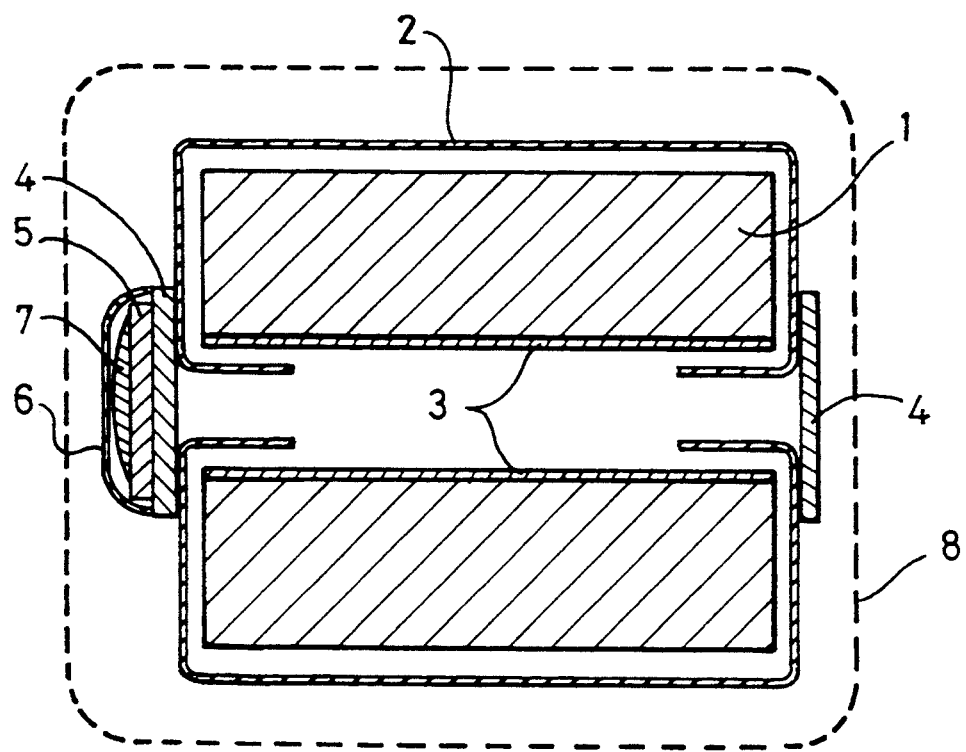
FIGS. 2 and 4 are vertical sectional views through the containers of FIGS. 1 and 3 respectively.

The toilet roll package of FIG. 1 comprises a conventional roll of perforated tissue paper 1 in a substantially airtight wrapping of a paper sleeve 2 having each of its ends gathered together into the tube 3 upon which the paper roll is wound. The ends of the sleeve are sealed with a paper disc 4 held in place by a PVA or other suitable adhesive. Such a wrapped toilet roll can be produced from conventional materials and by conventional techniques.

The toilet roll is provided with a scent disc 5 which can either be formed integrally with the end closure disc 4 or can be affixed as a separate component to the package. As shown, the disc 5 has a peel off outer plastic, paper or metal foil layer 6 which exposes a scent layer or coating applied to the disc 5. Alternatively, as shown the scent can be carried by a pad 7. The foil layer 6 is sealed to the periphery of the disc 5 so that with the disc 5 it totally encloses the area of the disc or pad 7 carrying the scent and a physical barrier is provided to escape of the scent from the enclosure. The scent can be applied to the disc 5 by any suitable technique, for example by spraying the fluid scent composition directly onto the disc and then applying the foil layer to prevent subsequent escape of the scent from the sealed disc.

When it is desired to activate the release of scent into the environment around the package, at least part of the foil layer is peeled back to expose the scent coated area of the disc or the pad 7. In this way the generally airtight packaging around the toilet paper itself is retained whilst the scent carried by the disc is exposed to escape into the environment.

When the toilet paper is required, the paper wrapping 2 is removed and discarded, thus exposing the toilet paper for access by a user. However, the scent composition has not been in contact with the paper and the user is not therefore at risk of an allergic reaction to the oils of the scent by direct contact therewith through the medium of the toilet paper.

In an alternative form of the package of FIG. 1, the scent disc 4 can carry a scent composition encapsulated in a suitable polymer or other coating which is applied to the outer face of disc 4. The disc is activated by rubbing a coin or the like across the disc to rupture the capsules or by the peeling action of the removal of a cover foil, strip or sheet overlying the capsules similar in function to the foil layer 7 described above.

The package of FIG. 1 can also or alternatively be wrapped in a removable outer paper or similar wrapping 8 which is removed to exposed the package and its scent disc 4 when it is desired to place the package in the toilet for imminent use and to expose the disc 4 to the environment.

Figure 3:
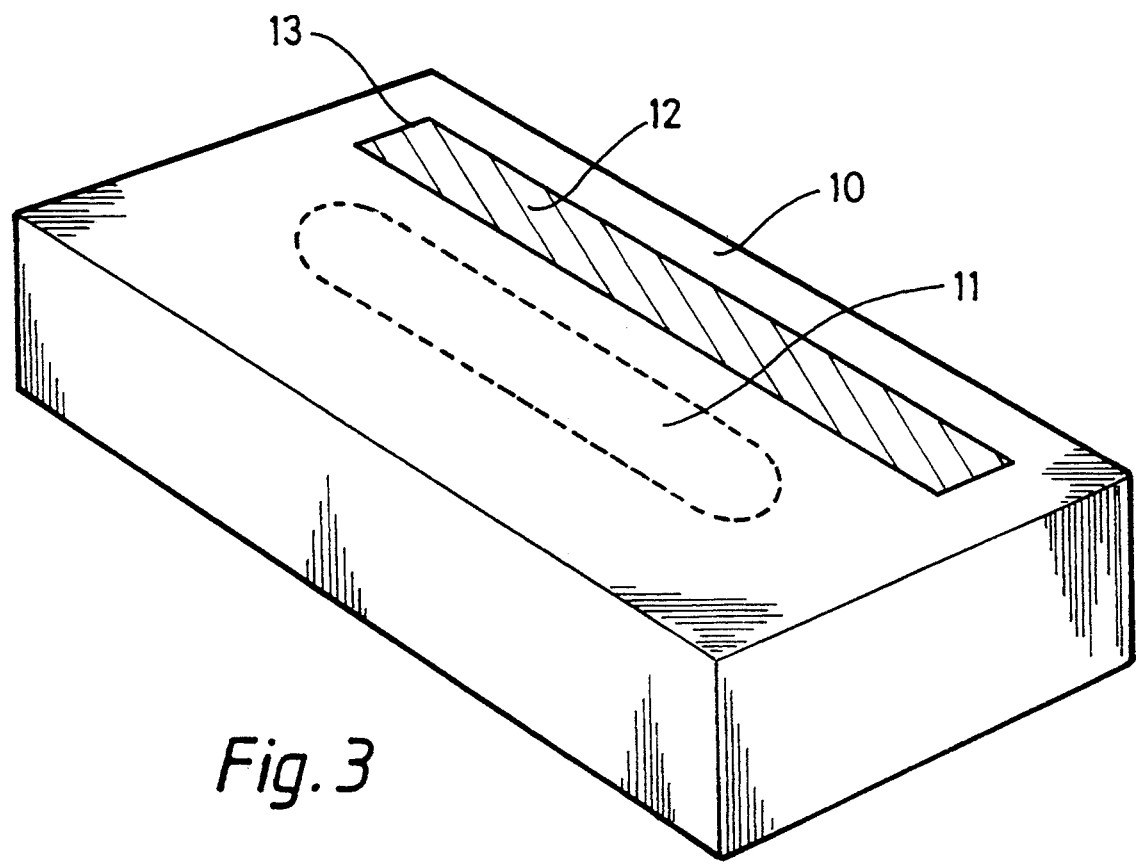
Figure 4:
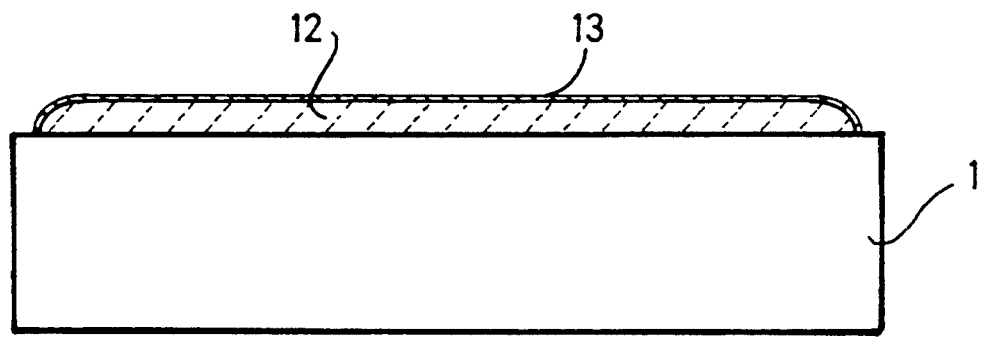

In the case of the package shown in FIGS. 3 and 4, the container is a cardboard or similar box 10 of conventional rectangular form containing interleaved single sheets of facial or other tissue. The box has a tear out section or panel 11 through which the sheets can be withdrawn by a user. Typically, this panel is formed by perforating the wall of the box around the periphery of the section or panel 11 so that the section or panel is releasably attached to the wall until it is required to remove it.

The box can carry a scent panel similar to either form of the scent disc 4 described above. Alternatively, a scent composition can be incorporated into the outer face of the cardboard from which the box is made, for example by incorporating a scent into an outer layer of a laminated construction; or capsules of the scent can be applied to an area of the outer face of the box for rupturing to release the scent. For example, such capsules can be applied to an area 12 of a wall of the container and covered with a removable panel 13, the removal of which ruptures the capsules to release the scent.

The box 10 can be wrapped in a secondary wrapping as described above if desired.

The outer face of the box 10 or the sleeve 2 can be printed with decorative motifs or the like to make the package more aesthetically attractive and can also carry the name of the manufacturer so that a user is reminded of the name of the manufacturer at all times. The invention can be applied to sample boxes or sachets of facial tissues with the scent disc or capsules containing a particular perfume which a perfume manufacturer wishes to promote.

I believe that the scent discs for use in the invention are novel and the invention provides a generally planar member adapted to be affixed to a substrate and having scent releasing means applied to one face thereof; and a scent impervious member applied over that face whereby the scent is released into the environment of the member by removal of part or all of the scent impervious member.

The impervious member is at least in part removably attached to the substrate, for example by means of a peripheral adhesive or other seal, so that the substrate and the impervious member for a total vapour imervious enclosure around the scent or other volatile material carried on the substrate so that there is formed a physical barrier to prevent escape of the volatile material from the substrate. Preferably, the scent or other volatile material is applied as a fluid to an area of the substrate and the impervious member is applied over at least that area of the substrate.

Preferably, the other face of the planar member is provided with an adhesive layer whereby the member can be affixed to a substrate. Preferably, the adhesive is a pressure sensitive adhesive applied as a coating to one face of the planar member and the scent releasing means is either a scent impregnated pad or an encapsulated scent composition applied as a layer to the other face of the planar member; and both the adhesive and scent releasing layers are covered by a removable cover, e.g. of paper, plastics or metal foil.

From a preferred aspect the invention also provides a means for releasing a volatile material into the environment of the means, which means comprises a first member having a volatile material applied to one face thereof; and a second member which is impervious to said volatile material applied over that said one face whereby the volatile material is wholly enclosed between said first and second members, said first and second members providing a physical barrier to the escape of said volatile material from said means, said second member being at least in part removable from said first member whereby said volatile material can be released into the environment of the first member by removal of at least part of the said second member.

What I claim is:

1. A flexible walled storage and transport container for a material, which container is adapted to have at least part of a wall thereof removed prior to use of the material so as to permit access to the material within the container for removal of the material from the container, characterised in that:
   a. the material within the container is toilet paper;
   b. the container is provided with a volatile material releasing means having no mechanical moving parts and adapted to release a volatile material externally of the container into the environment of the container;
   c. said releasing means is located on an outer wall of the container whereby it is adapted to release the volatile material substantially only externally of the container and substantially not into an interior of the container;
   d. the volatile material releasing means is adapted to be actuated prior to removal of the container wall to gain access to the contents within the container; and
   e. the volatile material releasing means is further characterized in that it comprises:
      (i) a generally planar vapour impermeable first layer to which a fluid consisting essentially of a liquid volatile material has been applied to a selected area of one face thereof; and
      (ii) a vapour impermeable second layer applied directly and without an intermediate layer over at least the said selected area of the first layer and removably secured to said first layer around at least the periphery thereof so as to form with the first layer a vapour impermeable enclosure for the fluid volatile material, whereby release of the volatile material from the first layer can be achieved by removing part or all of the said second layer to expose the area of the first layer carrying the fluid volatile material directly to the environment of the article so as to allow volatilization of the volatile material.

2. A container as claimed in claim 1, characterised in that the container comprises a paper or similar wrapping around a roll of toilet paper and the means for releasing the volatile material is carried on an exterior surface of the wrapping and is provided with means whereby the volatile material can be released from the means by a user when the container is exposed to a desired environment.

3. A container as claimed in claim 1, characterised in that the container comprises a generally tubular wrapping around a generally cylindrical roll of toilet paper, the generally tubular wrapping having open ends, the open ends of the wrapping being gathered together at each end of the roll to form a closure, the generally planar member of the volatile material releasing means being applied to at least one end of the resulting container.

4. A container as claimed in claim 1, characterised in that the first layer provides a vapour barrier interface between the volatile material and the container to which the volatile material releasing means is applied.

5. A container as claimed in claim 1, characterised in that the container is contained within an outer wrapping.

6. A container as claimed in claim 1, characterised in that the container is in the form of a box and the volatile material releasing means comprises a scent applied to an external wall of the container.

7. A container as claimed in claim 1, characterised in that the volatile material comprises a fragrance composition.

8. A unitary package characterised in that it comprises at least one container containing toilet paper, which at least one container is:
   a. adapted to have at least part of a wall thereof removed prior to use of the material so as to permit access to the material from the container;
   b. provided with a volatile material releasing means located on an outer wall of the container and having no mechanical moving parts and adapted to release a volatile material externally of the container into the environment of the container and substantially not into the interior of the container and being adapted to be actuated prior to removal of the container wall to gain access to the contents within the container;
   c. is contained within a substantially vapour impervious outer wrapping; and
   d. the volatile material releasing means comprises:
      (i) a generally planar vapour impermeable first layer to which a fluid consisting essentially of a liquid volatile material has been applied to a selected area of one face thereof; and
      (ii) a vapour impermeable second layer applied directly and without an intermediate layer over at least the said selected area of the first layer and removably secured to said first layer around at least the periphery thereof so as to form with the first layer a vapour impermeable enclosure for the fluid volatile material, whereby release of the volatile material from the first layer can be achieved by removing part or all of the said second layer to expose the area of the first layer carrying the fluid volatile material directly to the environment of the article so as to allow volatilization of the volatile material.

9. A generally planar volatile material releasing means adapted selectively to release a volatile material to the environment of the means by volatilization of the volatile material, characterised in that it comprises:
   a. a generally planar vapour impermeable first layer to which a fluid consisting essentially of a liquid volatile material has been applied to a selected area of one face thereof; and
   b. a vapour impermeable second layer applied directly and without an intermediate layer over at least the said selected area of the first layer and removably secured to said first layer around at least the periphery thereof so as to form with the first layer a vapour impermeable enclosure for the fluid volatile material, whereby release of the volatile material from the first layer can be achieved by removing part or all of the said second layer to expose the area of the first layer carrying the fluid volatile material directly to the environment of the article so as to allow volatilization of the volatile material.

10. A means as claimed in claim 9, wherein an adhesive is applied to the reverse face of the first or second layer to that carrying the volatile material, whereby the means can be affixed to another article.

11. A means as claimed in claim 9, wherein the volatile material consists essentially of a fragrance.

12. A means as claimed in claim 9 applied to an external wall of a flexible walled storage and transport container for a material, whereby the means is adapted to release the said volatile material externally of the container upon removal of said second layer.

13. A means as claimed in claim 12, wherein said second layer forms at least part of a closure to an aperture in a wall of the container through which aperture the material contained in the container is to be removed.

14. A generally planar volatile material releasing means adapted selectively to release a volatile material to the environment of the means by volatilization of the volatile material, characterised in that it comprises:
   a. generally planar vapour impermeable first layer having a fluid consisting essentially of a liquid volatile material impregnated at least in part into a selected area of one face thereof; and
   b. a vapour impermeable second layer applied directly and without an intermediate layer over at least the said selected area of the first layer and removably secured to said first layer around at least the periphery thereof so as to form with the first layer a vapour impermeable enclosure for the fluid volatile material, whereby release of the volatile material from the first layer can be achieved by removing part or all of the said second layer to expose the area of the first layer carrying the fluid volatile material directly to the environment of the article so as to allow volatilization of the volatile material.

* * * * *